(12) United States Patent
Zhang et al.

(10) Patent No.: US 12,367,754 B2
(45) Date of Patent: Jul. 22, 2025

(54) TRIGGERING METHOD AND TRIGGERING APPARATUS OF INTERVENTION PROMPT ON THE BASIS OF USER SMOKING BEHAVIOR RECORDS

(71) Applicant: MCNEIL AB, Helsingborg (SE)

(72) Inventors: Jing Zhang, Shanghai (CN); Congyang Wu, Shanghai (CN); Zhiyu Xu, Shanghai (CN); Licong Xing, Shanghai (CN); Ge Zhang, Shanghai (CN)

(73) Assignee: McNeil AB, Helsingborg (SE)

( * ) Notice: Subject to any disclaimer, the term of this patent is extended or adjusted under 35 U.S.C. 154(b) by 273 days.

(21) Appl. No.: 17/997,167

(22) PCT Filed: May 14, 2021

(86) PCT No.: PCT/CN2021/093799
§ 371 (c)(1),
(2) Date: Oct. 26, 2022

(87) PCT Pub. No.: WO2021/228220
PCT Pub. Date: Nov. 18, 2021

(65) Prior Publication Data
US 2023/0222890 A1    Jul. 13, 2023

(30) Foreign Application Priority Data

May 15, 2020   (CN) .......................... 202010417547.7

(51) Int. Cl.
*G08B 21/24*   (2006.01)
(52) U.S. Cl.
CPC .................................. *G08B 21/24* (2013.01)
(58) Field of Classification Search
CPC ........ G08B 21/24; G16H 50/30; G16H 20/70; G16H 20/30; A61B 5/1112; H04L 67/52; H04L 67/55; H04L 67/535
See application file for complete search history.

(56) References Cited

U.S. PATENT DOCUMENTS

| | | |
|---|---|---|
| 2015/0208723 A1 | 7/2015 | Glazer |
| 2016/0219931 A1 | 8/2016 | Doshi et al. |

(Continued)

FOREIGN PATENT DOCUMENTS

| | | |
|---|---|---|
| CN | 106983180 A | 7/2017 |
| CN | 201721019911 U | 3/2018 |

(Continued)

OTHER PUBLICATIONS

International search report and written opinion dated Aug. 25, 2021, for international application PCT/CN2021/093799.

*Primary Examiner* — Brian Wilson

(57) ABSTRACT

The present disclosure provides a triggering method of an intervention prompt on the basis of user smoking behavior records, comprising: receiving smoking behavior record data associated with a user, wherein the smoking behavior record data includes a plurality of smoking behavior records; analyzing the smoking behavior record data to determine smoking behavior location data associated with each of the plurality of smoking behavior records; calculating a distance between locations indicated by every two smoking behavior location data; recording a first number of smoking behavior records in which the distance is less than a first distance as a set of smoking behavior record data; in a case where the first number is greater than a first threshold, determining a prompt range on the basis of the smoking behavior location data associated with the set of smoking behavior record data, wherein the prompt range includes consecutive areas or spaces that are connected and further includes locations indicated by the respective smoking behavior location data associated with the set of smoking behavior record data; and triggering pushing of the intervention prompt if the user enters the prompt range from the outside.

21 Claims, 3 Drawing Sheets

(56) References Cited

U.S. PATENT DOCUMENTS

| | | |
|---|---|---|
| 2016/0371464 A1 | 12/2016 | Bricker |
| 2017/0071262 A1* | 3/2017 | Liu .......................... H04W 4/21 |
| 2018/0014729 A1 | 1/2018 | Reinhardt et al. |
| 2018/0068080 A1* | 3/2018 | Parate .................... G16H 20/70 |
| 2018/0188465 A1 | 7/2018 | Zer et al. |
| 2019/0261855 A1 | 8/2019 | Utley et al. |

FOREIGN PATENT DOCUMENTS

| | | |
|---|---|---|
| FR | 3008853 A | 1/2015 |
| JP | 2006277365 A | 10/2006 |
| JP | 2015060425 A | 3/2015 |
| JP | 2017091052 A | 5/2017 |
| WO | WO 2016/164484 A | 10/2016 |
| WO | WO 2019/051777 A | 3/2019 |

* cited by examiner

TRIGGERING METHOD AND TRIGGERING APPARATUS OF INTERVENTION PROMPT ON THE BASIS OF USER SMOKING BEHAVIOR RECORDS

CROSS-REFERENCE TO RELATED APPLICATIONS

This application is the national stage filing under 35 USC 371 of international application PCT/CN2021/093799 filed on May 14, 2021, which claims the benefit of Chinese patent application CN 202010417547.7 filed on May 15, 2020, the complete disclosures of which are hereby incorporated herein by reference for all purposes.

TECHNICAL FIELD

The present disclosure relates to a mechanism for triggering a smoking cessation intervention prompt. Specifically, the present disclosure relates to a triggering method of a smoking cessation intervention prompt on the basis of the cognitive behavior therapy (CBT) theory, and in particular relates to a triggering method of an intervention prompt on the basis of user smoking behavior records, a triggering apparatus of an intervention prompt on the basis of user smoking behavior records for performing the triggering method, and a corresponding computer-readable storage medium.

BACKGROUND OF THE INVENTION

The smoking cessation prompt function of the existing smoking cessation software mainly operates in the following modes:
  in the first mode, a prompt is pushed regularly by the software, for example, a prompt is sent out at 7 o'clock in the morning every day, the time when the user get up, or a prompt is pushed regularly at 9 am every morning, the time when the user arrives at the office;
  in the second mode, a prompt is triggered on a basis of a specific smoking site configured or located by the user, for example, the user inputs, into the software, location information of a company break room or smoking site where the user often smokes, then the software performs prompting regarding a specific smoking site on the basis of a comparison between the location thereof and the input location information; and
  in the third mode, a prompt is triggered on a basis of a specific smoking time configured by the user, for example, the user inputs, into the software, a time period during which the user often smokes, i.e., a time period within one hour after lunch (for example, the lunch time ends at 12 noon), then the software regularly pushes a smoking cessation prompt to the user at 11:30 am every day on the basis of the time acquired by a time unit thereof.

From the above three modes of smoking cessation prompting, it can be seen that the prompting modes in the prior art are all performed in a fixed manner, that is, the prompting is performed on the basis of either a fixed time or a specific fixed location, in which case the objective of performing an accurate and intelligent intervention on the basis of user smoking habits cannot be achieved.

SUMMARY

As stated above, the following technical problem exists in the prior art: in a conventional smoking cessation method, prompting is performed on the basis of either a fixed time or a specific fixed location, in which case the objective of performing an accurate and intelligent intervention on the basis of user smoking habits cannot be achieved. Furthermore, if the prompting is performed on the basis of a specific fixed location, due to insufficient accuracy of a positioning method such as GPS and the inherent problem of a conventional prompting mechanism and due to the consideration of only a single specific smoking site, the user receives prompts continuously if moving between smoking sites relatively close to each other, thereby degrading the actual effect of the prompting.

The objective of the present disclosure is to statistically analyze smoking habits of a user on the basis of personal smoking behavior records of the user, predict a time and a site with high possibility of user smoking, and prompt the user to undergo a smoking cessation intervention based on cognitive behavioral therapy by pushing a message, so as to avoid a smoking behavior.

In order to achieve the above objective, the inventor of the present disclosure has realized that the conventional mode of prompting on the basis of a specific smoking site has the following defects:
  first, the locating accuracy is insufficient, for example, current civilian GPS accuracy is generally about 10 meters, and under such the accuracy, prompting on the basis of a specific site may be insufficiently accurate;
  secondly, smoking frequency is not considered when prompting on the basis of a specific site is performed, that is, the prompting is performed indiscriminately without consideration of the craving of the user for smoking, in which case the prompting is excessively frequent, thereby significantly degrading the prompting effect; and
  furthermore, the existing smoking cessation prompting function cannot be adjusted dynamically, i.e, cannot be modified according to changes in external data, so that prompting on the basis of a specific site is inflexible and cannot be dynamically changed to match the actual situation, thereby necessarily degrading the effect of the smoking cessation prompting.

Regarding the above technical problems, on the basis of the above consideration, the inventor of the present disclosure proposed the following CBT theory-based mechanism for triggering a smoking cessation prompt. Specifically, the present disclosure relates to a triggering method of an intervention prompt on the basis of user smoking behavior records, the triggering method comprising:
  receiving smoking behavior record data associated with a user, wherein the smoking behavior record data includes a plurality of smoking behavior records;
  analyzing the smoking behavior record data to determine smoking behavior location data associated with each of the plurality of smoking behavior records;
  calculating a distance between locations indicated by every two smoking behavior location data;
  recording a first number of smoking behavior records in which the distance is less than a first distance as a set of smoking behavior record data;
  in a case where the first number is greater than a first threshold, determining a prompt range on the basis of the smoking behavior location data associated with the set of smoking behavior record data, wherein the prompt range includes a consecutive communicating area or space and further includes locations indicated by the respective smoking behavior location data associated with the set of smoking behavior record data; and triggering pushing of the intervention prompt if the user enters the prompt range from the outside.

In the triggering method of an intervention prompt on the basis of user smoking behavior records provided by the present disclosure, a set of smoking behavior record data is collected according to a distance between smoking locations, then a prompt range including these locations is calculated on the basis of the collected set of smoking behavior record data, and prompting is performed on the basis of a specific prompt range. On the one hand, excessively frequent prompting is avoided, achieving the technical effect of enabling a single prompt to be more accurate; on the other hand, the defect of an inaccurate locating prompt range resulting from the excessively low accuracy of a conventional locating means is eliminated. In addition, the impact of smoking frequency is fully considered, and prompting is performed only for gathering smoking sites in which smoking frequency is higher than the first threshold, thereby increasing the pertinence of an intervention prompt, necessarily leading to an increase in user attention, and ultimately achieving the objective of improving the effect of smoking cessation.

In an embodiment of the present disclosure, determining a prompt range on the basis of the smoking behavior location data associated with the set of smoking behavior record data comprises:

computing a physical center point of the smoking behavior location data associated with the set of smoking behavior record data, wherein the prompt range includes a range centering on the physical center point and having a radius of a second distance, and the second distance is not less than a distance between the physical center point and a smoking behavior location that is farthest from the physical center point and indicated by the set of smoking behavior record data.

In this way, the calculation of the prompt range is further simplified by computing the physical center point including these locations on the basis of the collected set of smoking behavior record data, so that the triggering method of an intervention prompt on the basis of user smoking behavior records provided by the present disclosure is easier to be implemented.

In an embodiment of the present disclosure, determining a prompt range on the basis of the smoking behavior location data associated with the set of smoking behavior record data comprises:

determining a first prompt range on the basis of each of the locations indicated by the respective smoking behavior location data associated with the set of smoking behavior record data, wherein the prompt range consists of a plurality of the first prompt ranges.

In this way, the impact of the respective smoking behavior location data on the final prompt range can be more accurate, so that a calculated prompt range is more pertinent, thereby improving the pertinence of a location-based intervention prompt.

In an embodiment of the present disclosure, the triggering method further comprises:

analyzing the smoking behavior record data and determining smoking behavior time data associated with the respective smoking behavior record data;

calculating the smoking counts in predetermined time periods on the basis of the smoking behavior time data;

recording predetermined time periods in which the smoking counts are greater than a second threshold; and triggering pushing of the intervention prompts before start time points of the predetermined time periods.

On the basis of the location-based prompting, the present disclosure further discloses time-based prompting, wherein, by sending prompts again before the start of time periods in which smoking frequency is greater than the second threshold, the pertinence of an intervention prompt can be increased, necessarily leading to an increase in user attention, and ultimately achieving the objective of improving the effect of smoking cessation.

In an embodiment of the present disclosure, the triggering method further comprises:

analyzing the smoking behavior record data and determining smoking behavior time data associated with the respective smoking behavior record data;

calculating the smoking counts in predetermined time periods on the basis of the smoking behavior time data;

ranking the predetermined time periods in a descending order according to the smoking counts; and triggering pushing of the intervention prompts before start time points of a predetermined number of highest-ranking predetermined time periods.

On the basis of the location-based prompting, the present disclosure further discloses time-based prompting, wherein, by sending prompts again before the start of a predetermined number of highest-ranking time periods, the pertinence of an intervention prompt can be increased, necessarily leading to an increase in user attention, and ultimately achieving the objective of improving the effect of smoking cessation.

In an embodiment of the present disclosure, the form of the intervention prompt includes a voice prompt, a video prompt, an image prompt, and a text prompt, and the form of the intervention prompt is related to specific time indicated by the predetermined time period.

As a living organism, humans have different degrees of feedback or attention to various prompt forms in different time periods. For example, in the morning, a user tends to read a text prompt carelessly but readily accepts a voice or image prompt, whereas, before sleeping at night, the user readily accepts a video or text prompt. On this basis, the inventor of the present disclosure creatively conceives the idea of designing the form of an intervention prompt to be related to specific time indicated by the predetermined time period, so as to increase user attention and ultimately achieve the objective of improving the effect of smoking cessation.

In an embodiment of the present disclosure, the triggering method further comprises:

receiving user data associated with the user;

determining a nicotine dependence degree of the user on the basis of the user data; and determining the type of the intervention prompt on the basis of the nicotine dependence degree of the user, wherein the type of the intervention prompt includes a positive message, a neutral message, and a negative message.

As a living organism, humans have different degrees of attention to different types of prompts. For example, a user with a high nicotine dependence degree needs to be informed of the severe consequences of smoking, so the proportion of negative messages is correspondingly higher than that for a user with a low or middle nicotine dependence degree. For a user with a low nicotine dependence degree, encouraging positive messages have a better prompting effect. Therefore, for the user with a low nicotine dependence degree, the proportion of positive messages is correspondingly higher than that for a user with a middle or high nicotine dependence degree.

The second aspect of the present disclosure provides a triggering apparatus of an intervention prompt on the basis of user smoking behavior records, the triggering apparatus comprising:
  a data receiving module, configured to receive smoking behavior record data associated with a user, wherein the smoking behavior record data includes a plurality of smoking behavior records;
  an analysis module, configured to analyze the smoking behavior record data to determine smoking behavior location data associated with each of the plurality of smoking behavior records;
  a first calculation module, configured to calculate a distance between locations indicated by every two smoking behavior location data;
  a grouping module, configured to record a first number of smoking behavior records in which the distance is less than a first distance as a set of smoking behavior record data;
  a second calculation module, configured to, in a case where the first number is greater than a first threshold, determine a prompt range on the basis of location data associated with the set of smoking behavior record data, wherein the prompt range includes a consecutive communicating area or space and further includes locations indicated by the respective smoking behavior location data associated with the set of smoking behavior record data; and
  a trigger module, configured to trigger pushing of the intervention prompt if the user enters the prompt range from the outside.

In an embodiment of the present disclosure, determining a prompt range on the basis of the smoking behavior location data associated with the set of smoking behavior record data comprises:
  computing a physical center point of the smoking behavior location data associated with the set of smoking behavior record data, wherein the prompt range includes a range centering on the physical center point and having a radius of a second distance, and the second distance is not less than a distance between the physical center point and a smoking behavior location that is farthest from the physical center point and indicated by the set of smoking behavior record data.

In an embodiment of the present disclosure, determining a prompt range on the basis of the smoking behavior location data associated with the set of smoking behavior record data comprises:
  determining a first prompt range on the basis of each of the locations indicated by the respective smoking behavior location data associated with the set of smoking behavior record data, wherein the prompt range consists of a plurality of the first prompt ranges.

In an embodiment of the present disclosure, the analysis module is further configured to analyze the smoking behavior record data and determine smoking behavior time data associated with the respective smoking behavior record data; the first calculation module is further configured to calculate the smoking counts in predetermined time periods on the basis of the smoking behavior time data; and the triggering apparatus further comprises:
  a recording module, configured to record predetermined time periods in which the smoking counts are greater than a second threshold; and
  a first time trigger module, configured to trigger pushing of the intervention prompts before start time points of the predetermined time periods.

In an embodiment of the present disclosure, the analysis module is further configured to analyze the smoking behavior record data and determine smoking behavior time data associated with the respective smoking behavior record data; the first calculation module is further configured to calculate the smoking counts in predetermined time periods on the basis of the smoking behavior time data; and the triggering apparatus further comprises:
  a ranking module, configured to rank the predetermined time periods in a descending order according to the smoking counts; and
  a second time trigger module, configured to trigger pushing of the intervention prompts before start time points of a predetermined number of highest-ranking predetermined time periods.

In an embodiment of the present disclosure, the form of the intervention prompt includes a voice prompt, a video prompt, an image prompt, and a text prompt, and the form of the intervention prompt is related to specific time indicated by the predetermined time period.

In an embodiment of the present disclosure, the data receiving module is further configured to receive user data associated with the user; and the triggering apparatus further comprises:
  a third calculation module, configured to determine a nicotine dependence degree of the user on the basis of the user data; and
  an intervention prompt type determination module, configured to determine the type of the intervention prompt on the basis of the nicotine dependence degree of the user, wherein the type of the intervention prompt includes a positive message, a neutral message, and a negative message.

The third aspect of the present disclosure provides a tangible computer-readable storage medium, the storage medium including instructions for executing a triggering method of an intervention prompt on the basis of user smoking behavior records, the instructions, when executed, causing a processor of a computer to be at least used to:
  receive smoking behavior record data associated with a user, wherein the smoking behavior record data includes a plurality of smoking behavior records;
  analyze the smoking behavior record data to determine smoking behavior location data associated with each of the plurality of smoking behavior records;
  calculate a distance between locations indicated by every two smoking behavior location data;
  record a first number of smoking behavior records in which the distance is less than a first distance as a set of smoking behavior record data;
  in a case where the first number is greater than a first threshold, determine a prompt range on the basis of the smoking behavior location data associated with the set of smoking behavior record data, wherein the prompt range includes a consecutive communicating area or space and further includes locations indicated by the respective smoking behavior location data associated with the set of smoking behavior record data; and
  trigger pushing of the intervention prompt if the user enters the prompt range from the outside.

In an embodiment of the present disclosure, determining a prompt range on the basis of the smoking behavior location data associated with the set of smoking behavior record data comprises:

computing a physical center point of the smoking behavior location data associated with the set of smoking behavior record data, wherein the prompt range includes a range centering on the physical center point and having a radius of a second distance, and the second distance is not less than a distance between the physical center point and a smoking behavior location that is farthest from the physical center point and indicated by the set of smoking behavior record data.

In an embodiment of the present disclosure, determining a prompt range on the basis of the smoking behavior location data associated with the set of smoking behavior record data comprises:

determining a first prompt range on the basis of each of the locations indicated by the respective smoking behavior location data associated with the set of smoking behavior record data, wherein the prompt range consists of a plurality of the first prompt ranges.

In an embodiment of the present disclosure, the instructions, when executed, further cause the processor of the computer to be at least used to:

analyze the smoking behavior record data and determine smoking behavior time data associated with the respective smoking behavior record data;

calculate the smoking counts in predetermined time periods on the basis of the smoking behavior time data;

record predetermined time periods in which the smoking counts are greater than a second threshold; and trigger pushing of the intervention prompts before start time points of the predetermined time periods.

In an embodiment of the present disclosure, the instructions, when executed, further cause the processor of the computer to be at least used to:

analyze the smoking behavior record data and determine smoking behavior time data associated with the respective smoking behavior record data;

calculate the smoking counts in predetermined time periods on the basis of the smoking behavior time data;

rank the predetermined time periods in a descending order according to the smoking counts; and trigger the pushing of the intervention prompts before start time points of a predetermined number of highest-ranking predetermined time periods.

In an embodiment of the present disclosure, the form of the intervention prompt includes a voice prompt, a video prompt, an image prompt, and a text prompt, and the form of the intervention prompt is related to specific time indicated by the predetermined time period.

In an embodiment of the present disclosure, the instructions, when executed, further cause the processor of the computer to be at least used to:

receive user data associated with the user;

determine a nicotine dependence degree of the user on the basis of the user data; and determine the type of the intervention prompt on the basis of the nicotine dependence degree of the user, wherein the type of the intervention prompt includes a positive message, a neutral message, and a negative message.

To sum up, the three aspects of the present disclosure provide a triggering method of an intervention prompt on the basis of user smoking behavior records, a triggering apparatus of an intervention prompt on the basis of user smoking behavior records and for executing the triggering method, and a corresponding computer-readable storage medium. A set of smoking behavior record data is collected according to a distance between smoking locations, then a prompt range including these locations is calculated on the basis of the collected set of smoking behavior record data, and prompting is performed on the basis of a specific prompt range. On the one hand, excessively frequent prompting is avoided, achieving the technical effect of enabling a single prompt to be more accurate; on the other hand, the defect of an inaccurate locating prompt range resulting from the excessively low accuracy of a conventional locating means is eliminated. In addition, the impact of smoking frequency is fully considered, and prompting is performed only for gathering smoking sites in which smoking frequency is higher than the first threshold, thereby increasing the pertinence of an intervention prompt, necessarily leading to an increase in user attention, and ultimately achieving the objective of improving the effect of smoking cessation. Other advantages of the present disclosure are further described below.

BRIEF DESCRIPTION OF THE DRAWINGS

With reference to the following detailed description in combination with the accompanying drawings, the features, advantages, and other aspects of the embodiments of the present disclosure become more obvious. Several embodiments of the present disclosure are shown in an exemplary rather than restrictive manner herein. Regarding the accompanying drawings.

DETAILED DESCRIPTION

Figure 1:
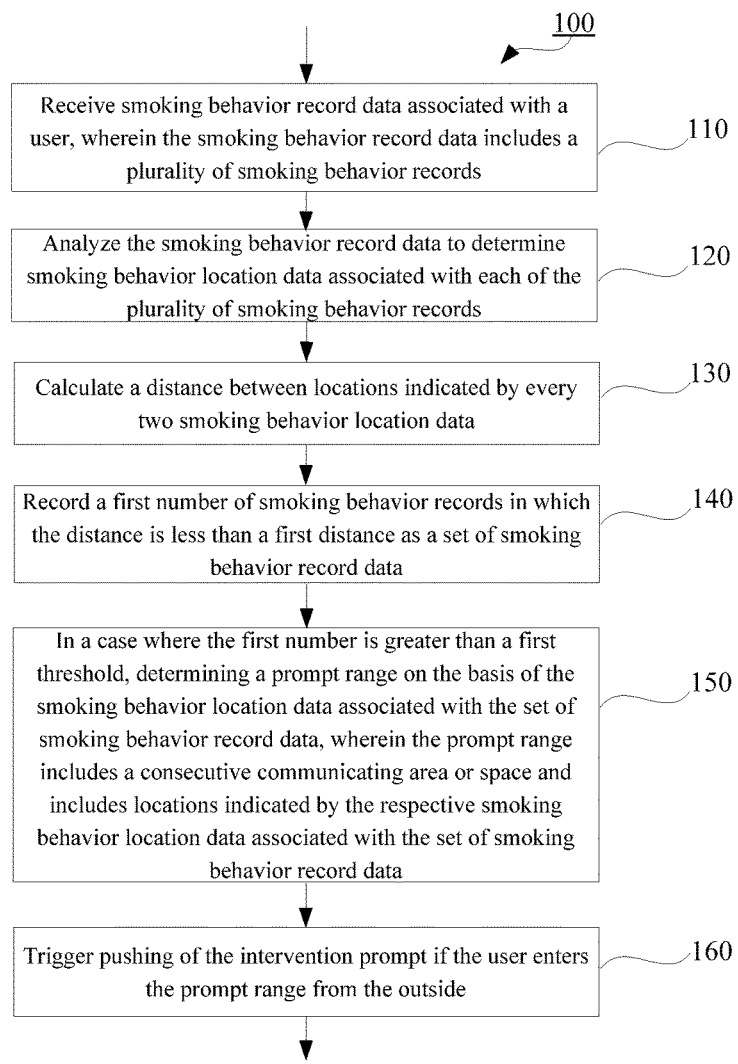
FIG. 1 illustrates a flowchart of a method 100 for triggering an intervention prompt on the basis of user smoking behavior records according to an embodiment of the present disclosure.

Various exemplary embodiments of the present disclosure are described in detail below with reference to the accompanying drawings. Although the exemplary methods and apparatus described below include software and/or firmware executed on hardware in other components, it should be noted that these examples are merely illustrative and should not be considered limiting. For example, it is contemplated that any or all hardware, software, and firmware components may be implemented exclusively in hardware, exclusively in software, or in any combination of hardware and software. Accordingly, although the exemplary methods and apparatus are described below, it should be readily understood by those skilled in the art that the examples provided are not intended to limit manners for implementing these methods and apparatus.

Moreover, the flowcharts and block diagrams in the accompanying drawings illustrate a system architecture, a function, and an operation that can be possibly implemented by the methods and systems according to various embodiments of the present disclosure. It should be noted that the functions noted in the blocks may also occur in an order different from that noted in the drawings. For example, two blocks represented in succession may actually be substantially executed in parallel, or they may sometimes be executed in the reverse order, depending upon the function involved. It should also be noted that each block of the flowcharts and/or block diagrams, and combinations of blocks in the flowcharts and/or block diagrams, may be implemented using dedicated hardware-based systems that perform the specified functions or operations, or may be implemented using a combination of dedicated hardware and computer instructions.

Before introducing the detailed description of the present disclosure in detail, some terms used in the present disclosure are first described.

In the present disclosure, the term "physical center point" refers to a center point of locations indicated by a set of smoking behavior record data. For example, on a two-dimensional plane, the average longitude of a whole set of points is assigned to the longitude of a physical center point, and the average latitude of the whole set of points is assigned to the latitude of the physical center point. Similarly, in a three-dimensional space, the average longitude of a whole set of points is assigned to the longitude of a physical center point, the average latitude of the whole set of points is assigned to the latitude of the physical center, and the average height of the whole set of points is assigned to the height of the physical center point.

In the present disclosure, the term "prompt range" refers to a two-dimensional planar area or a three-dimensional spatial area, wherein pushing of the intervention prompt is triggered if a user enters the prompt range from the outside.

In the present disclosure, the term "smoking behavior record data" refers to smoking behavior records associated with a specific user, and can be either static data of smoking behavior records inputted by the user in a preparation stage or dynamic data of smoking behavior records generated during an entire smoking cessation process.

Before the introduction of the prompting mechanism proposed in the present disclosure, the applicant of the present disclosure hopes to first introduce several models that will be described as follows, specifically relating to a user model, an intervention model, and a message model. Other models having low relevance are mentioned but not described in detail.

User Model

In an application, a user undergoes user portrait classification (gender, smoking cessation experience, BMI index, nicotine dependence degree, etc.) by a questionnaire test, and records smoking behaviors (information such as smoking time, GPS longitude, GPS latitude, the smoking count, the degree of craving, etc.) by a function of smoking recording. In the subsequent triggering method of an intervention prompt on the basis of user smoking behavior records, some of the said parameters are used for making decisions, so as to perform targeted intervention prompting for a specific user.

Intervention Model

Smoking site-based intervention model: statistical analysis is performed on smoking density points according to the latitude and longitude of GPS data collected from user smoking behavior records, wherein it is defined that in a matrix of a range within 200 meters (the first distance), the number of smoking recording points is greater than or equal to 5. A center point is computed on the basis of these smoking record locations, to perform subsequent location-based intervention. If the user enters from the outside into a range centering on the center point and having a radius of 200 meters (the second distance), a push condition is formed. According to this algorithm rule, a plurality of user smoking density center points can be computed so as to perform an accurate intervention. Compared with a single fixed location mode, the 200-meter range statistical mode can minimize locating errors and enable an intervention prompt to be more accurate, reasonable, and effective.

The smoking density point algorithm refers to an algorithm for calculating points classified as a set of smoking behavior record data:

Matrices are enumerated by means of permutation and combination. First, a first point is computed and matched with other points, so as to find all points within 200 meters away from the first point, for example, points 1, 2, 4, 5, 7, 8, 9, 12, 22, 23, 24, 25, 27, 29, 33, 34, 35, 37, etc. Then a second point is computed and matched with other points, so as to find all points within 200 meters away from the second point, for example, points 2, 1, 4, 5, 12, 22, 23, etc. Then a third point is computed and matched with other points, so as to find all points within 200 meters away from the third point, for example, points 4, 1, 2, 5, 12, 22, 23, etc. Then a fourth point is computed and matched with other points, so as to find all points within 200 meters away from the fourth point, points such as 5, 1, 2, 4, 12, 33, 34, 35, etc. Then a fifth point is computed and matched with other points, so as to find all points within 200 meters away from the fifth point, for example, points 12, 1, 2, 4, 5, 36, 37, 41, etc. By analogy, these matrices are integrated to obtain intersections, and if the intersections occur at more than five of the aforementioned points, these points are considered to be the desired density points, such as 1, 2, 4, 5, etc.

In summary, FIG. 1 illustrates a flowchart of a method 100 for triggering an intervention prompt on the basis of user smoking behavior records according to an embodiment of the present disclosure. It can be seen from the figure that the method 100 for triggering an intervention prompt on the basis of user smoking behavior records according to an the present disclosure at least includes the following six steps.

First, in method step 110, smoking behavior record data associated with a user is received, wherein the smoking behavior record data includes a plurality of smoking behavior records, thereby providing a basis for subsequent determination. For example, the smoking behavior record data includes 20 smoking behavior records. Next, the smoking behavior record data is analyzed in method step 120 to determine the smoking behavior location data associated with each of the plurality of smoking behavior records. Since the smoking behavior record data not only includes location data, but may also include information such as time data, people with whom the user smokes, etc., it is necessary to analyze the smoking behavior record data to extract the smoking behavior location data associated with each of the plurality of smoking behavior records. Next, in method step 130, a distance between locations indicated by every two smoking behavior location data is calculated. Herein, as shown in the detailed example introduced above, each smoking behavior record is traversed to determine the distance between every two smoking locations, which may be 50 meters, 80 meters, 170 meters, 185 meters, 5 kilometers, and so on. Then, in method step 140, a first number of smoking behavior records in which the distance is less than a first distance is recorded as a set of smoking behavior record data. For example, an example of the first distance herein can be selected as 200 meters; in this case, an associated smoking location point at a distance of less than 200 meters from one of the location points is classified as a gathering point. For example, of the 20 smoking behavior records, 7 records indicate locations around the residence, 8 records indicate locations around the office, 2 records indicate sites such as a subway station on the way to the office, and 3 records indicate locations in a shopping mall. Next, in method step 150, in a case where the first number is greater than a first threshold, a prompt range is determined on the basis of the smoking behavior location data associated with the set of smoking behavior record data, wherein the prompt range includes a consecutive communicating area or space and further includes locations indicated by the respective smoking behavior location data associated with the set of smoking behavior record data. Herein, an example of the first threshold can be selected to be 5 times. Then, as shown in the above example, two smoking gathering points are obtained, i.e., residence with 7 times of smoking and office with 8 times of smoking. A prompt range is formed on the basis of the two sites, wherein the prompt range includes a consecutive communicating area or space and further includes locations indicated by the respective smoking behavior location data associated with 7 pieces of smoking behavior record data pertaining to the residence or further includes locations indicated by the respective smoking behavior location data associated with 8 pieces of smoking behavior record data pertaining to the office. Correspondingly, since the selected first threshold is 5 times, no prompt range is formed for a site such as a subway station on the way to the office where a smoking record is 2 times or for a shopping mall where a smoking record is 3 times. Finally, in method step 160, pushing of the intervention prompt is triggered if the user enters the prompt range from the outside. In the triggering method of an intervention prompt on the basis of user smoking behavior records provided by the present disclosure, a set of smoking behavior record data is collected according to a distance between smoking locations, then a prompt range including these locations is calculated on the basis of the collected set of smoking behavior record data, and prompting is performed on the basis of a specific prompt range. On the one hand, excessively frequent prompting is avoided, achieving the technical effect of enabling a single prompt to be more accurate; on the other hand, the defect of an inaccurate locating prompt range resulting from the excessively low accuracy of a conventional locating means is eliminated. In addition, the impact of smoking frequency is fully considered, and prompting is performed only for gathering smoking sites in which smoking frequency is higher than the first threshold, thereby increasing the pertinence of an intervention prompt, necessarily leading to an increase in user attention, and ultimately achieving the objective of improving the effect of smoking cessation.

In an embodiment of the present disclosure, determining a prompt range on the basis of the smoking behavior location data associated with the set of smoking behavior record data in method step 150 includes: computing a physical center point of the smoking behavior location data associated with the set of smoking behavior record data, wherein the prompt range includes a range centering on the physical center point and having a radius of a second distance, and the second distance is not less than a distance between the physical center point and a smoking behavior location that is farthest from the physical center point and indicated by the set of smoking behavior record data. For example, if the locations indicated by the location data are on a plane, i.e., on a two-dimensional plane, the average longitude of a whole set of points is assigned to the longitude of the physical center point, and the average latitude of the whole set of points is assigned to the latitude of the physical center point. Similarly, in a three-dimensional space such as an office building, i.e., in a three-dimensional space, the average longitude of a whole set of points is assigned to the longitude of the physical center point, the average latitude of the whole set of points is assigned to the latitude of the physical center, and the average height of the whole set of points is assigned to the height of the physical center point. In this way, the calculation of the prompt range is further simplified by computing the physical center point including these locations on the basis of the collected set of smoking behavior record data, so that the triggering method of an intervention prompt on the basis of user smoking behavior records provided by the present disclosure is easier to be implemented.

In an embodiment of the present disclosure, determining a prompt range on the basis of the smoking behavior location data associated with the set of smoking behavior record data in method step 150 further includes: determining a first prompt range on the basis of each of the locations indicated by the respective smoking behavior location data associated with the set of smoking behavior record data, wherein the prompt range consists of a plurality of the first prompt ranges. For example, regarding the gathering point selected previously, the distance between two adjacent smoking locations is required to be less than 200 meters. Thus, by regarding each location in a set of smoking behavior record data as the center of a circle or a sphere having a radius greater than 100 meters, multiple prompt ranges connected to each other can form an entirety. On a two-dimensional plane, such prompt ranges can be formed by drawing circles to form connected planar areas. Correspondingly, in a spatial area, prompt ranges connected to each other can be necessarily formed by drawing spheres. In another implementation, any two points can be connected together to form a closed area or space, and the area or space can be regarded as a prompt range herein. Preferably, the area or space can be extended outward by a range of, for example, 5 meters, so as to improve the tolerance of such prompt range, thereby improving the accuracy of an intervention prompt. In this way, the impact of the respective smoking behavior location data on the final prompt range can be more accurate, so that the calculated prompt range is more pertinent, thereby improving the pertinence of the location-based prompting.

Figure 2:
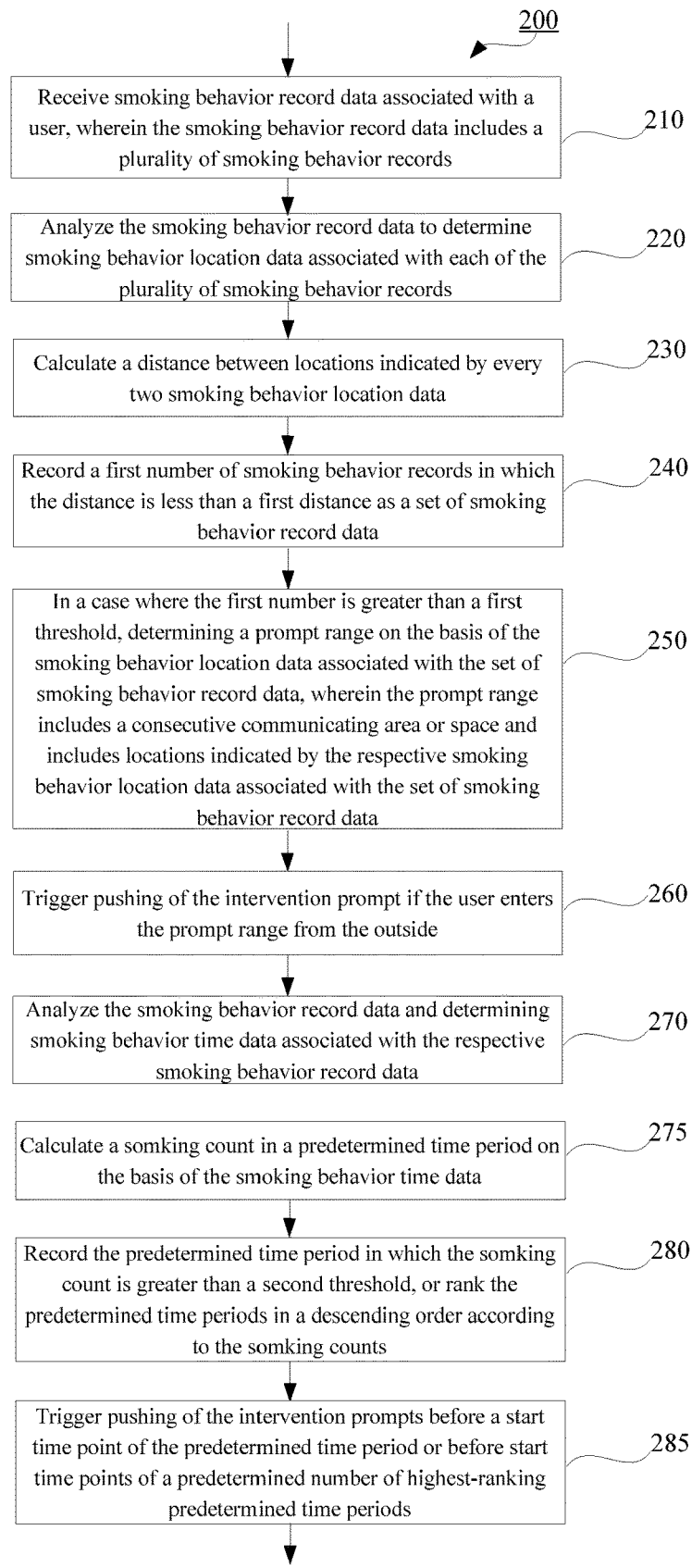
FIG. 2 illustrates a flowchart of a method 200 for triggering an intervention prompt on the basis of user smoking behavior records according to another embodiment of the present disclosure.

FIG. 2 illustrates a flowchart of a method 200 for triggering an intervention prompt on the basis of user smoking behavior records according to another embodiment of the present disclosure. It can be seen from FIG. 2 that, in addition to the six steps in FIG. 1, the method 200 for triggering an intervention prompt on the basis of user smoking behavior records according to another embodiment of the present disclosure further includes four additional steps. The four additional steps are used to implement additional time-based prompting.

Method steps 210-260 correspond to method steps 110-160 in FIG. 1 and thus are not described herein. For brevity, only the last four steps are described herein. That is, in method step 270, the triggering method further analyzes the smoking behavior record data and determines smoking behavior time data associated with the respective smoking behavior record data. As stated above, since the smoking behavior record data not only includes location data, but may also include information such as time data, people with whom the user smokes, etc., it is necessary to analyze the smoking behavior record data so as to determine the smoking behavior time data associated with the respective smoking behavior record data. Next, in method step 275, the smoking counts in predetermined time periods are calculated on the basis of the smoking behavior time data. Then, in method step 280, predetermined time periods in which the smoking counts are greater than a second threshold are recorded. For example, the smoking count is set to 3 times herein; that is, predetermined time periods in which the smoking counts are greater than the second threshold, i.e., 3 times, are compiled and recorded. Alternatively, the predetermined time periods can be herein ranked in a descending order according to the smoking counts. For example, the top three or top five predetermined time periods are selected, that is, predetermined time periods that require prompts are selected in method step 280. Finally, in method step 285, pushing of the intervention prompts is triggered before start time points of the predetermined time periods or pushing of the intervention prompts is triggered before start time points of a predetermined number of highest-ranking predetermined time periods. On the basis of the location-based prompting, the present disclosure further discloses time-based prompting, wherein, by sending prompts again before the start of time periods in which smoking frequency is greater than the second threshold or by sending prompts again before the start of a predetermined number of highest-ranking time periods, the pertinence of an intervention prompt can be further increased, necessarily leading to an increase in user attention, and ultimately achieving the objective of improving the effect of smoking cessation.

Specifically, a smoking time-based intervention model is as follows: the smoking count in a time period starting and finishing on the hour is calculated on the basis of the smoking time data collected from the user smoking behavior records, for example, 1:00-2:00, 2:00-3:00, etc.; and then the smoking counts in different time periods starting and finishing on the hour in a day are calculated and ranked. For a time period with a high smoking count, intervention prompting is performed 30 minutes before the top of the hour, and the number of times of prompting is gradually reduced with the extension of smoking cessation duration. Specific prompting configurations are shown in Table 1 below:

TABLE 1

Relationship between the number of times of prompting and smoking cessation duration

| Smoking cessation lasting 0 day to 1 week | Smoking cessation lasting 1 week to 4 weeks | Smoking cessation lasting 4 weeks to 6 weeks | Smoking cessation lasting 6 weeks to 12 weeks |
|---|---|---|---|
| 3 times a day (top three time periods in which smoking is performed most frequently) | 2 times a day (top two time periods in which smoking is performed most frequently) | 1 time a day (top one time period in which smoking is performed most frequently) | 3 times a week (top one time periods with in which smoking is performed most frequently) |

For example, a user is currently in a smoking cessation stage of 0 day to 1 week. On the basis of data collected previously, it is determined by analysis that, the user smokes most frequently in time periods of 8-9 o'clock, 11-12 o'clock, and 15-16 o'clock in a day. Therefore, an intervention prompt is separately pushed at 7:30, 10:30, and 14:30.

In such the time-based intervention prompt push mode, the push time can be dynamically analyzed and adjusted according to the input of the user smoking behaviors, and the user habit can be representatively reflected using statistical data, and an accurate and reasonable prediction can be thereby performed.

In addition, there are various forms of intervention prompts. As a living organism, humans have different degrees of feedback or attention to various prompt forms in different time periods. For example, in the morning, a user tends to read a text prompt carelessly but readily accepts a voice or image prompt, whereas, before sleeping at night, the user readily accepts a video or text prompt. On this basis, the inventor of the present disclosure creatively conceives the idea of designing the form of an intervention prompt to be related to specific time indicated by the predetermined time period, so as to increase user attention and ultimately achieve the objective of improving the effect of smoking cessation. On the basis of such consideration, in an embodiment of the present disclosure, the form of the intervention prompt includes a voice prompt, a video prompt, an image prompt, and a text prompt, and the form of the intervention prompt is related to specific time indicated by the predetermined time period.

Furthermore, as a living organism, humans have different degrees of attention to different types of prompts. For example, a user with a high nicotine dependence degree needs to be informed of the severe consequences of smoking, so the proportion of negative messages is correspondingly higher than that for a user with a low or middle nicotine dependence degree. For a user with a low nicotine dependence degree, encouraging positive messages have a better prompting effect. Therefore, for the user with a low nicotine dependence degree, the proportion of positive messages is correspondingly higher than that for a user with a middle or high nicotine dependence degree. On this basis, in an embodiment of the present disclosure, the triggering method further includes: receiving user data associated with the user; determining a nicotine dependence degree of the user on the basis of the user data; and determining the type of the intervention prompt on the basis of the nicotine dependence degree of the user, wherein the type of the intervention prompt includes a positive message, a neutral message, and a negative message.

For example, a questionnaire result indicates that the user is mildly dependent on nicotine and smokes frequently in the morning, so it is necessary to push an intervention prompt to the user at a certain time in the morning. From the analysis of the above two tables, it can be seen that voice messages or image messages need to be randomly screened out from all pushed messages, wherein the ratio of the number of the voice messages to the number of the image messages is 80%:20%=4:1, the voice messages consist of positive messages, neutral messages, and negative messages at a ratio of 60%:20%:20%=3:1:1, and the image messages also consist of positive messages, neutral messages, and negative messages at a ratio of 60%:20%:20%=3:1:1. Finally, a message is selected randomly from the screened-out messages for pushing. On the basis of the above consideration, the prompt messages pushed according to the intervention push model are classified, according to the content, into positive content, neutral content, and negative content. Each content is classified, according to the presentation form, into four types: voice, video, text, and image. Message pushing is classified according to user model classifications and pushing time periods, and specific rules are shown in Table 2 below:

TABLE 2

Relationship between the type of intervention prompt for the user and nicotine dependence degree

| User model type | Pushing of positive messages | Pushing of neutral messages | Pushing of negative messages |
| --- | --- | --- | --- |
| Users with low nicotine dependence degree | 60% | 20% | 20% |
| Users with middle nicotine dependence degree | 50% | 20% | 30% |
| Users with high nicotine dependence degree | 40% | 20% | 40% |

Furthermore, in the morning, a user tends to read a text prompt carelessly but readily accepts a voice or image prompt, whereas, before sleeping at night, the user readily accepts a video or text prompt. On this basis, the inventor of the present disclosure creatively conceives the idea of designing the form of an intervention prompt to be related to specific time indicated by the predetermined time period, so as to increase user attention and ultimately achieve the objective of improving the effect of smoking cessation.

TABLE 3

Relationship between the form of intervention prompt for the user and specific time period

| Pushing time period | Voice | Video | Text | Image |
| --- | --- | --- | --- | --- |
| Morning | 80% | / | / | 20% |
| Noon | / | / | 50% | 50% |
| Evening | / | 50% | 50% | / |

A learning algorithm of the intervention model described above: the type of smoking cessation attribute of users, the type of smoking cessation solution to which the users better adapt to, and messages and content in which the users are more interested, and success factors of subsequent smoking cessation are obtained by buried point analysis and user feedback data collection, and combined to form a machine learning algorithm, and an algorithm threshold of the intervention model is dynamically adjusted.

Figure 3:
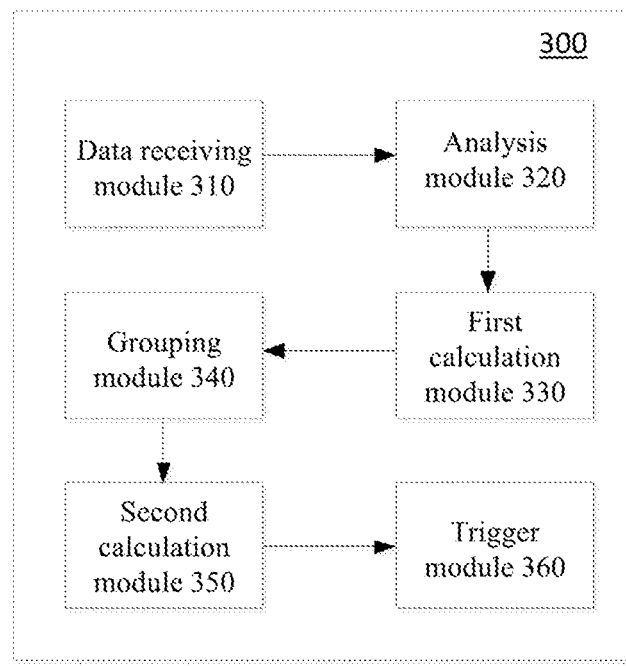
FIG. 3 illustrates a schematic block diagram of an apparatus 300 for triggering an intervention prompt on the basis of user smoking behavior records according to an embodiment of the present disclosure.

The above triggering method of an intervention prompt on the basis of user smoking behavior records may be implemented by means of general computer equipment (such as a smart phone, a tablet computer, a laptop, or a desktop computers) or dedicated computer equipment (such as a smoking cessation smart bracelet or a dedicated smoking cessation device). Such computer equipment necessarily includes a triggering apparatus of an intervention prompt on the basis of user smoking behavior records. FIG. 3 illustrates a schematic block diagram of an apparatus 300 for triggering an intervention prompt on the basis of user smoking behavior records according to an embodiment of the present disclosure. It can be seen from FIG. 3 that the triggering apparatus includes: a data receiving module 310, configured to receive smoking behavior record data associated with a user, wherein the smoking behavior record data includes a plurality of smoking behavior records; an analysis module 320, configured to analyze the smoking behavior record data to determine smoking behavior location data associated with each of the plurality of smoking behavior records; a first calculation module 330, configured to calculate a distance between locations indicated by every two smoking behavior location data; a grouping module 340, configured to record a first number of smoking behavior records in which the distance is less than a first distance as a set of smoking behavior record data; a second calculation module 350, configured to, in a case where the first number is greater than a first threshold, determine a prompt range on the basis of the smoking behavior location data associated with the set of smoking behavior record data, wherein the prompt range includes a consecutive communicating area or space and further includes locations indicated by the respective smoking behavior location data associated with the set of smoking behavior record data; and a trigger module 360, configured to trigger pushing of the intervention prompt if the user enters the prompt range from the outside. Optionally, in an embodiment of the present disclosure, determining a prompt range on the basis of the smoking behavior location data associated with the set of smoking behavior record data includes: computing a physical center point of the smoking behavior location data associated with the set of smoking behavior record data, wherein the prompt range includes a range centering on the physical center point and having a radius of a second distance, and the second distance is not less than a distance between the physical center point and a smoking behavior location that is farthest from the physical center point and indicated by the set of smoking behavior record data. Optionally or alternatively, in an embodiment of the present disclosure, determining a prompt range on the basis of the smoking behavior location data associated with the set of smoking behavior record data further includes: determining a first prompt range on the basis of each of the locations indicated by the respective smoking behavior location data associated with the set of smoking behavior record data, wherein the prompt range consists of a plurality of the first prompt ranges.

In addition, in an embodiment of the present disclosure, the analysis module is further configured to analyze the smoking behavior record data and determine smoking behavior time data associated with the respective smoking behavior record data; the first calculation module is further configured to calculate the smoking counts in predetermined time periods on the basis of the smoking behavior time data; and the triggering apparatus further includes: a recording module, configured to record predetermined time periods in which the smoking counts are greater than a second threshold; and a first time trigger module, configured to trigger pushing of the intervention prompts before start time points of the predetermined time periods. Optionally or alternatively, in an embodiment of the present disclosure, the analysis module is further configured to analyze the smoking behavior record data and determine smoking behavior time data associated with the respective smoking behavior record data; the first calculation module is further configured to calculate the smoking counts in predetermined time periods on the basis of the smoking behavior time data; and the triggering apparatus further includes: a ranking module, configured to rank the predetermined time periods in a descending order according to the smoking counts; and a second time trigger module, configured to trigger pushing of the intervention prompts before start time points of a predetermined number of highest-ranking predetermined time periods.

In addition, in an embodiment of the present disclosure, the form of the intervention prompt includes a voice prompt, a video prompt, an image prompt, and a text prompt, and the form of the intervention prompt is related to specific time indicated by the predetermined time period. In an embodiment of the present disclosure, the data receiving module is further configured to receive user data associated with the user; and the triggering apparatus further includes: a third calculation module, configured to determine a nicotine dependence degree of the user on the basis of the user data; and an intervention prompt type determination module, configured to determine the type of the intervention prompt on the basis of the nicotine dependence degree of the user, wherein the type of the intervention prompt includes a positive message, a neutral message, and a negative message.

In addition, alternatively, the method described above may be implemented by a computer program product, i.e., a computer-readable storage medium. The computer program product may include a computer-readable storage medium, carrying computer-readable program instructions thereon for performing various aspects of the present disclosure. The computer-readable storage medium may be a tangible device that can hold and store instructions for use by an instruction execution device. The computer-readable storage medium may be, for example, but is not limited to, an electrical storage device, a magnetic storage device, an optical storage device, an electromagnetic storage device, a semiconductor storage device, or any suitable combination of the foregoing. More specific examples (the list of which is not exhaustive) of the computer-readable storage medium include: a portable computer diskette, a hard disk, a random access memory (RAM), a read-only memory (ROM), an erasable programmable read-only memory (EPROM or flash memory), a static random access memory (SRAM), a portable compact disc read-only memory (CD-ROM), a digital versatile disc (DVD), a memory stick, a floppy disk, a mechanical coding device, a punched card or protruding structure in a groove, for example, having instructions stored thereon, and any suitable combination of the foregoing. The computer-readable storage medium used herein is not to be construed as an instantaneous signal per se, such as a radio wave or another freely propagating electromagnetic wave, an electromagnetic wave propagating through a waveguide or other transmission medium (e.g., a light pulse passing through a fiber optic cable), or an electrical signal transmitted through a wire.

Figure 4:
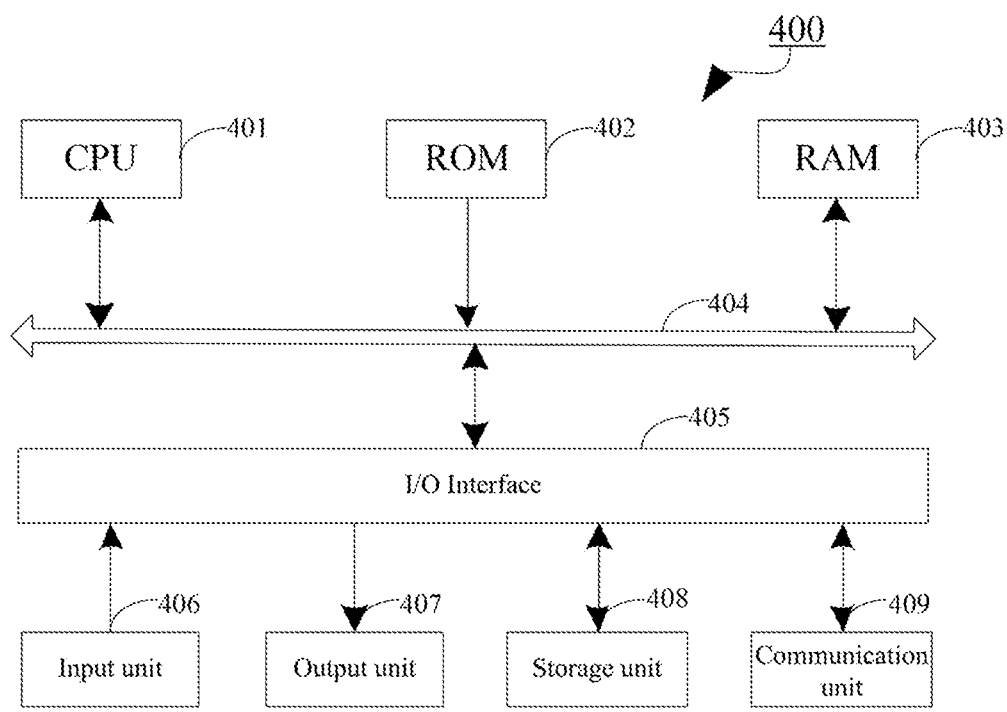
FIG. 4 illustrates a schematic block diagram of an apparatus 400 for triggering an intervention prompt on the basis of user smoking behavior records according to another embodiment of the present disclosure.

FIG. 4 illustrates a schematic block diagram of an apparatus 400 for triggering an intervention prompt on the basis of user smoking behavior records according to an embodiment of the present disclosure. It can be understood that, the triggering apparatus 400 may be implemented to implement the functionality of the method 100 for triggering an intervention prompt on the basis of user smoking behavior records in FIG. 1 or the method 200 for triggering an intervention prompt on the basis of user smoking behavior records in FIG. 2. It can be seen from FIG. 4 that the apparatus 400 includes a central processing unit (CPU) 401 (for example, a processor), which can perform various appropriate actions and processes according to computer program instructions stored in the read-only memory (ROM) 402 or computer program instructions loaded into the random access memory (RAM) 403 from the storage unit 408. Various programs and data required for operation of the triggering apparatus 400 may also be stored in the RAM 403. The CPU 401, ROM 402, and RAM 403 are connected to each other by a bus 404. An input/output (I/O) interface 405 is also connected to the bus 404.

A plurality of components in the triggering apparatus 400 are connected to the I/O interface 405, including: an input unit 406, for example, a keyboard, a mouse, etc.; an output unit 407, for example, various types of displays, speakers, etc.; a storage unit 408, for example, a magnetic disk, an optical disk, etc.; and a communication unit 409, for example, a network card, a modem, a wireless communication transceiver, etc. The communication unit 409 allows the apparatus 400 to exchange information/data with other devices over a computer network, for example the Internet, and/or various telecommunications networks.

In summary, the third aspect of the present disclosure provides a tangible computer-readable storage medium, the storage medium including instructions for executing a triggering method of an intervention prompt on the basis of user smoking behavior records, the instructions, when executed, causing a processor of a computer to be at least used to: receive smoking behavior record data associated with a user, wherein the smoking behavior record data includes a plurality of smoking behavior records; analyze the smoking behavior record data to determine smoking behavior location data associated with each of the plurality of smoking behavior records; calculate a distance between locations indicated by every two smoking behavior location data; record a first number of smoking behavior records in which the distance is less than a first distance as a set of smoking behavior record data; in a case where the first number is greater than a first threshold, determine a prompt range on the basis of the smoking behavior location data associated with the set of smoking behavior record data, wherein the prompt range includes a consecutive communicating area or space and further includes locations indicated by the respective smoking behavior location data associated with the set of smoking behavior record data; and trigger pushing of the intervention prompt if the user enters the prompt range from the outside.

In an embodiment of the present disclosure, determining a prompt range on the basis of the smoking behavior location data associated with the set of smoking behavior record data includes: computing a physical center point of the smoking behavior location data associated with the set of smoking behavior record data, wherein the prompt range includes a range centering on the physical center point and having a radius of a second distance, and the second distance is not less than a distance between the physical center point and a smoking behavior location that is farthest from the physical center point and indicated by the set of smoking behavior record data.

In an embodiment of the present disclosure, determining a prompt range on the basis of the smoking behavior location data associated with the set of smoking behavior record data further includes: determining a first prompt range on the basis of each of the locations indicated by the respective smoking behavior location data associated with the set of smoking behavior record data, wherein the prompt range consists of a plurality of the first prompt ranges.

In an embodiment of the present disclosure, the instructions, when executed, further cause the processor of the computer to be at least used to: analyze the smoking behavior record data and determine smoking behavior time data associated with the respective smoking behavior record data; calculate the smoking counts in predetermined time periods on the basis of the smoking behavior time data; record predetermined time periods in which the smoking counts are greater than a second threshold; and trigger pushing of the intervention prompts before start time points of the predetermined time periods.

In an embodiment of the present disclosure, the instructions, when executed, further cause the processor of the computer to be at least used to: analyze the smoking behavior record data and determine smoking behavior time data associated with the respective smoking behavior record data; calculate the smoking counts in predetermined time periods on the basis of the smoking behavior time data; rank the predetermined time periods in a descending order according to the smoking counts; and trigger pushing of the intervention prompts before start time points of a predetermined number of highest-ranking predetermined time periods.

In an embodiment of the present disclosure, the form of the intervention prompt includes a voice prompt, a video prompt, an image prompt, and a text prompt, and the form of the intervention prompt is related to specific time indicated by the predetermined time period.

In an embodiment of the present disclosure, the instructions, when executed, further cause the processor of the computer to be at least used to: receive user data associated with the user; determine a nicotine dependence degree of the user on the basis of the user data; and determine the type of the intervention prompt on the basis of the nicotine dependence degree of the user, wherein the type of the intervention prompt includes a positive message, a neutral message, and a negative message.

To sum up, the three aspects of the present disclosure provide a triggering method of an intervention prompt on the basis of user smoking behavior records, a triggering apparatus of an intervention prompt on the basis of user smoking behavior records and for executing the triggering method, and a corresponding computer-readable storage medium. A set of smoking behavior record data is collected according to a distance between smoking locations, then a prompt range including these locations is calculated on the basis of the collected set of smoking behavior record data, and prompting is performed on the basis of a specific prompt range. On the one hand, excessively frequent prompting is avoided, achieving the technical effect of enabling a single prompt to be more accurate; on the other hand, the defect of an inaccurate locating prompt range resulting from the excessively low accuracy of a conventional locating means is eliminated. In addition, the impact of smoking frequency is fully considered, and prompting is performed only for gathering smoking sites in which smoking frequency is higher than the first threshold, thereby increasing the pertinence of an intervention prompt, necessarily leading to an increase in user attention, and ultimately achieving the objective of improving the effect of smoking cessation.

The various methods described above, such as the method 100 for triggering an intervention prompt on the basis of user smoking behavior records or the method 200 for triggering an intervention prompt on the basis of user smoking behavior records, may be executed by the processing unit 401. For example, in some embodiments, the method 100 for triggering an intervention prompt on the basis of user smoking behavior records or the method 200 for triggering an intervention prompt on the basis of user smoking behavior records may be implemented as a computer software program, which is tangibly contained in a machine-readable medium, such as the storage unit 408. In some embodiments, a part of or the entire computer program may be loaded and/or installed onto the triggering apparatus 400 via the ROM 402 and/or the communication unit 409. When the computer program is loaded onto the RAM 403 and executed by the processor CPU 401, one or more actions or steps of the method 100 for triggering an intervention prompt on the basis of user smoking behavior records or the method 200 for triggering an intervention prompt on the basis of user smoking behavior records described above may be executed.

Generally speaking, various example embodiments of the present disclosure may be implemented in hardware or dedicated circuitry, software, firmware, logic, or any combination thereof. Some aspects may be implemented in hardware, while other aspects may be implemented in firmware or software that may be executed by a controller, a microprocessor, or other computing devices. While aspects of embodiments of the present disclosure are illustrated or described as block diagrams, flowcharts, or represented using some other graphical representations, it will be understood that the blocks, apparatuses, systems, techniques, or methods described herein may be implemented as non-limiting examples in hardware, software, firmware, dedicated circuits or logic, general-purpose hardware or controllers, or other computing devices, or some combination thereof.

Although it has been described above that various example embodiments of the present disclosure can be implemented in hardware or dedicated circuits, the aforementioned data processing device for the block chain can be implemented in the form of hardware or software. This is because: in the 1990s, a technical improvement can easily be a hardware improvement (for example, an improvement in circuit structures such as diodes, transistors, and switches) or a software improvement (for example, an improvement in method flows). However, with continued development of technology, many improvements in method flows today can almost be achieved by programming an improved method flow into a hardware circuit. In other words, a corresponding hardware circuit structure is obtained by programming different programs for the hardware circuit, that is, the hardware circuit structure is changed. Therefore, such improvements in method flows can also be regarded as direct improvements in the hardware circuit structure. Therefore, it cannot be said that an improvement in a method flow cannot be implemented by a hardware entity module. For example, a programmable logic device (PLD) (such as a field programmable gate array (FPGA)) is an integrated circuit whose logic function is determined by programming the device by a user. The designer performs programming by himself to "integrate" a digital system on a piece of programmable logic device, without the need for a dedicated integrated circuit chip designed and manufactured by a chip manufacturer. Also, instead of making an integrated circuit chip manually, this programming is also implemented with "logic compiler" software similar to the software compiler used in program development writing, while the raw code to be compiled has to be written in a particular programming language, referred to as the Hardware Description Language (HDL), and HDL also does not have only one kind, but rather multiple kinds, such as Advanced Boolean Expression Language (ABEL), Altera Hardware Description Language (AHDL), Confluence, Cornell University Programming Language (CUPL), HDCal, Java Hardware Description Language (JHDL), Lava, Lola, MyHDL, PALASM, Ruby Hardware Description Language (RHDL), etc., The Very-High-Speed Integrated Circuit Hardware Description Language (VHDL) and Verilog are currently most commonly used. It should also be clear to those skilled in the art that the hardware circuit for implementing the logic method flow can be easily obtained by only slightly logically programming a method flow using the above several hardware description languages and programming the method flow into an integrated circuit.

Computer-readable program instructions or computer program products for executing various aspects of the present disclosure can also be stored in the cloud. When invoking is required, a user can access the computer-readable program instructions stored on the cloud for executing an aspect of the present disclosure via a mobile Internet, a solid network, or other networks, thereby implementing the technical solutions disclosed according to various aspects of the present disclosure.

The above descriptions are merely optional embodiments of the present disclosure, and are not intended to limit the embodiments of the present disclosure. For those skilled in the art, the embodiments of the present disclosure may have various changes and modifications. Any modifications, equivalent substitutions, improvements, etc. made within the spirit and principle of the embodiments of the present disclosure shall fall within the protection scope of the embodiments of the present disclosure.

While embodiments of the present disclosure have been described with reference to several specific embodiments, it should be understood that embodiments of the disclosure are not limited to the specific embodiments disclosed. Embodiments of the present disclosure are intended to cover various modifications and equivalent arrangements included within the spirit and scope of the appended claims. The scope of the claims is accorded the broadest interpretation, thereby including all such modifications as well as equivalent structures and functions.

What is claimed is:

1. A triggering method of an intervention prompt on the basis of user smoking behavior records, comprising:
    receiving smoking behavior record data associated with a user, wherein the smoking behavior record data includes a plurality of smoking behavior records;
    analyzing the smoking behavior record data to determine smoking behavior location data associated with each of the plurality of smoking behavior records;
    calculating a distance between locations indicated by every two smoking behavior location data;
    recording a first number of smoking behavior records in which the distance is less than a first distance as a set of smoking behavior record data;
    in a case where the first number is greater than a first threshold, determining a prompt range on the basis of the smoking behavior location data associated with the set of smoking behavior record data, wherein the prompt range includes a consecutive communicating area or space and includes locations indicated by the respective smoking behavior location data associated with the set of smoking behavior record data; and
    triggering pushing of the intervention prompt if the user enters the prompt range from the outside.

2. The triggering method according to claim 1, wherein determining a prompt range on the basis of the smoking behavior location data associated with the set of smoking behavior record data further comprises:
    computing a physical center point of the smoking behavior location data associated with the set of smoking behavior record data, wherein the prompt range includes a range centering on the physical center point and having a radius of a second distance, and the second distance is not less than a distance between the physical center point and a smoking behavior location that is farthest from the physical center point and indicated by the set of smoking behavior record data.

3. The triggering method according to claim 1, wherein determining a prompt range on the basis of the smoking behavior location data associated with the set of smoking behavior record data further comprises:
    determining a first prompt range on the basis of each of the locations indicated by the respective smoking behavior location data associated with the set of smoking behavior record data, wherein the prompt range consists of a plurality of the first prompt ranges.

4. The triggering method according to claim 1, wherein the triggering method further comprises:
    analyzing the smoking behavior record data and determining smoking behavior time data associated with the respective smoking behavior record data;
    calculating a smoking count in a predetermined time period on the basis of the smoking behavior time data;
    recording the predetermined time period in which the smoking count is greater than a second threshold; and
    triggering pushing of the intervention prompt before a start time point of the predetermined time period.

5. The triggering method according to claim 1, wherein the triggering method further comprises:
    analyzing the smoking behavior record data and determining smoking behavior time data associated with the respective smoking behavior record data;
    calculating smoking counts in predetermined time periods on the basis of the smoking behavior time data;
    ranking the predetermined time periods in a descending order according to the smoking counts; and
    triggering pushing of the intervention prompts before start time points of a predetermined number of highest-ranking predetermined time periods.

6. The triggering method according to claim 1, wherein the form of the intervention prompt includes a voice prompt, a video prompt, an image prompt, and a text prompt, and the form of the intervention prompt is related to a specific time indicated by a predetermined time period.

7. The triggering method according to claim 1, the triggering method further comprising:
    receiving user data associated with the user;
    determining a nicotine dependence degree of the user on the basis of the user data; and
    determining the type of the intervention prompt on the basis of the nicotine dependence degree of the user, wherein the type of the intervention prompt includes a positive message, a neutral message, and a negative message.

8. A triggering apparatus of an intervention prompt on the basis of user smoking behavior records, the triggering apparatus comprising:
    a data receiving module, configured to receive smoking behavior record data associated with a user, wherein the smoking behavior record data includes a plurality of smoking behavior records;
    an analysis module, configured to analyze the smoking behavior record data to determine smoking behavior location data associated with each of the plurality of smoking behavior records;
    a first calculation module, configured to calculate a distance between locations indicated by every two smoking behavior location data;
    a grouping module, configured to record a first number of smoking behavior records in which the distance is less than a first distance as a set of smoking behavior record data;
    a second calculation module, configured to, in a case where the first number is greater than a first threshold, determine a prompt range on the basis of location data associated with the set of smoking behavior record data, wherein the prompt range includes a consecutive communicating area or space and includes locations indicated by the respective smoking behavior location data associated with the set of smoking behavior record data; and a trigger module, configured to trigger pushing of the intervention prompt if the user enters the prompt range from the outside.

9. The triggering apparatus according to claim 8, wherein determining a prompt range on the basis of the smoking behavior location data associated with the set of smoking behavior record data comprises:

computing a physical center point of the smoking behavior location data associated with the set of smoking behavior record data, wherein the prompt range includes a range centering on the physical center point and having a radius of a second distance, and the second distance is not less than a distance between the physical center point and a smoking behavior location that is farthest from the physical center point and indicated by the set of smoking behavior record data.

10. The triggering apparatus according to claim 8, wherein determining a prompt range on the basis of the smoking behavior location data associated with the set of smoking behavior record data comprises:

determining a first prompt range on the basis of each of the locations indicated by the respective smoking behavior location data associated with the set of smoking behavior record data, wherein the prompt range consists of a plurality of the first prompt ranges.

11. The triggering apparatus according to claim 8, wherein the analysis module is further configured to analyze the smoking behavior record data and determine smoking behavior time data associated with the respective smoking behavior record data; the first calculation module is further configured to calculate a smoking count in a predetermined time period on the basis of the smoking behavior time data; and the triggering apparatus further comprises:

a recording module, configured to record the predetermined time period in which the smoking count is greater than a second threshold; and a first time trigger module, configured to trigger pushing of the intervention prompt before a start time point of the predetermined time period.

12. The triggering apparatus according to claim 8, wherein the analysis module is further configured to analyze the smoking behavior record data and determine smoking behavior time data associated with the respective smoking behavior record data; the first calculation module is further configured to calculate smoking counts in predetermined time periods on the basis of the smoking behavior time data; and the triggering apparatus further comprises:

a ranking module, configured to rank the predetermined time periods in a descending order according to the smoking counts; and a second time trigger module, configured to trigger pushing of the intervention prompts before start time points of a predetermined number of highest-ranking predetermined time periods.

13. The triggering apparatus according to claim 8, wherein the form of the intervention prompt includes a voice prompt, a video prompt, an image prompt, and a text prompt, and the form of the intervention prompt is related to a specific time indicated by a predetermined time period.

14. The triggering apparatus according to claim 8, wherein the data receiving module is further configured to receive user data associated with the user; and the triggering apparatus further comprises:

a third calculation module, configured to determine a nicotine dependence degree of the user on the basis of the user data; and an intervention prompt type determination module, configured to determine the type of the intervention prompt on the basis of the nicotine dependence degree of the user, wherein the type of the intervention prompt includes a positive message, a neutral message, and a negative message.

15. A non-transitory computer-readable storage medium, the storage medium including instructions for performing a triggering method of an intervention prompt on the basis of user smoking behavior records, the instructions, when executed, causing a processor of a computer to be at least used to:

receive smoking behavior record data associated with a user, wherein the smoking behavior record data includes a plurality of smoking behavior records;

analyze the smoking behavior record data to determine smoking behavior location data associated with each of the plurality of smoking behavior records;

calculate a distance between locations indicated by every two smoking behavior location data;

record a first number of smoking behavior records in which the distance is less than a first distance as a set of smoking behavior record data;

in a case where the first number is greater than a first threshold, determine a prompt range on the basis of the smoking behavior location data associated with the set of smoking behavior record data, wherein the prompt range includes a consecutive communicating area or space and includes locations indicated by the respective smoking behavior location data associated with the set of smoking behavior record data; and trigger pushing of the intervention prompt if the user enters the prompt range from the outside.

16. The computer-readable storage medium according to claim 15, wherein determining a prompt range on the basis of the smoking behavior location data associated with the set of smoking behavior record data comprises:

computing a physical center point of the smoking behavior location data associated with the set of smoking behavior record data, wherein the prompt range includes a range centering on the physical center point and having a radius of a second distance, and the second distance is not less than a distance between the physical center point and a smoking behavior location that is farthest from the physical center point and indicated by the set of smoking behavior record data.

17. The computer-readable storage medium according to claim 15, wherein determining a prompt range on the basis of the smoking behavior location data associated with the set of smoking behavior record data comprises:

determining a first prompt range on the basis of each of the locations indicated by the respective smoking behavior location data associated with the set of smoking behavior record data, wherein the prompt range consists of a plurality of the first prompt ranges.

18. The computer-readable storage medium according to claim 15, wherein the instructions, when executed, further cause the processor of the computer to be at least used to:

analyze the smoking behavior record data and determine smoking behavior time data associated with the respective smoking behavior record data;

calculate a smoking count in a predetermined time period on the basis of the smoking behavior time data;

record the predetermined time period in which the smoking count is greater than a second threshold; and trigger pushing of the intervention prompt before a start time point of the predetermined time period.

19. The computer-readable storage medium according to claim 15, wherein the instructions, when executed, further cause the processor of the computer to be at least used to:

analyze the smoking behavior record data and determine smoking behavior time data associated with the respective smoking behavior record data;

calculate smoking counts in predetermined time periods on the basis of the smoking behavior time data;

rank the predetermined time periods in a descending order according to the smoking counts; and trigger pushing of the intervention prompts before start time points of a predetermined number of highest-ranking predetermined time periods.

20. The computer-readable storage medium according to claim 15, wherein the form of the intervention prompt includes a voice prompt, a video prompt, an image prompt, and a text prompt, and the form of the intervention prompt is related to a specific time indicated by a predetermined time period.

21. The computer-readable storage medium according to claim 15, wherein the instructions, when executed, further cause the processor of the computer to be at least used to:

receive user data associated with the user;

determine a nicotine dependence degree of the user on the basis of the user data; and determine the type of the intervention prompt on the basis of the nicotine dependence degree of the user, wherein the type of the intervention prompt includes a positive message, a neutral message, and a negative message.

* * * * *